United States Patent
Dempsey (10) Patent No.: US 9,254,188 B2
(45) Date of Patent: Feb. 9, 2016

(54) KITS, COMPONENTS AND METHODS FOR TISSUE RECONSTRUCTION

(71) Applicant: Cook Biotech Incorporated, West Lafayette, IN (US)

(72) Inventor: Ryan Dempsey, Carmel, IN (US)

(73) Assignee: Cook Biotech Incorporated, West Lafayette, IN (US)

( * ) Notice: Subject to any disclaimer, the term of this patent is extended or adjusted under 35 U.S.C. 154(b) by 0 days.

(21) Appl. No.: 13/835,539

(22) Filed: Mar. 15, 2013

(65) Prior Publication Data

US 2013/0211519 A1 Aug. 15, 2013

Related U.S. Application Data

(63) Continuation of application No. PCT/US2011/054333, filed on Sep. 30, 2011.

(60) Provisional application No. 61/388,944, filed on Oct. 1, 2010.

(51) Int. Cl.
| | |
|---|---|
| *A61F 2/12* | (2006.01) |
| *A61F 2/52* | (2006.01) |
| *A61B 19/00* | (2006.01) |
| *A61B 17/00* | (2006.01) |
| *A61B 17/32* | (2006.01) |

(52) U.S. Cl.
CPC . *A61F 2/12* (2013.01); *A61B 19/54* (2013.01); *A61B 2017/00792* (2013.01); *A61B 2017/00796* (2013.01); *A61B 2017/320052* (2013.01); *A61B 2019/545* (2013.01); *A61F 2240/005* (2013.01)

(58) Field of Classification Search
CPC .................................. A61F 2/12; A61F 2/52
USPC ............ 623/7, 8, 23.64, 23.67; 128/888–890; 450/81
See application file for complete search history.

(56) References Cited

U.S. PATENT DOCUMENTS

| | | | |
|---|---|---|---|
| 4,640,288 | A | 2/1987 | Hattori |
| 4,778,465 | A | 10/1988 | Wilkins |
| 4,870,977 | A | 10/1989 | Imonti |
| 5,032,103 | A | 7/1991 | Larsson |
| 5,743,272 | A | 4/1998 | Kocher, Jr. |

(Continued)

FOREIGN PATENT DOCUMENTS

| | | |
|---|---|---|
| EP | 1 197 198 A1 | 4/2002 |
| EP | 2 133 062 | 12/2009 |

(Continued)

OTHER PUBLICATIONS

Salgarello, Marzia et al., "The use of a silicone nipple shield as a protective device in nipple reconstruction," Journal of Plastic, Resonstructive and Aesthetic Surgery, 2000, xx, 1-2.

(Continued)

*Primary Examiner* — Yashita Sharma
(74) *Attorney, Agent, or Firm* — Woodard Emhardt Moriarty McNett & Henry LLP (57) ABSTRACT

Described are components, component combinations, kits and methods useful for creating reconstructed tissue structures such as reconstructed nipple structures. Novel combinations are described involving surgical marking templates, implants having features correlated to the templates, and/or post-surgical shields.

15 Claims, 5 Drawing Sheets

(56) References Cited

U.S. PATENT DOCUMENTS

| | | |
|---|---|---|
| 5,772,654 A | 6/1998 | Leyva |
| 5,782,672 A | 7/1998 | Woodley |
| D398,398 S | 9/1998 | Taggerty |
| 5,937,863 A * | 8/1999 | Knowlton ..................... 128/898 |
| 6,071,309 A | 6/2000 | Knowlton |
| 6,338,665 B1 | 1/2002 | Dawson et al. |
| 7,008,409 B2 | 3/2006 | Speizio et al. |
| 7,175,502 B2 | 2/2007 | Clark |
| 7,938,122 B2 | 5/2011 | Clark |
| 2003/0014108 A1 | 1/2003 | Lauren |
| 2003/0073930 A1 | 4/2003 | Morrissey et al. |
| 2006/0106329 A1* | 5/2006 | Hammer et al. ................ 602/61 |
| 2006/0157065 A1 | 7/2006 | Rohrig |
| 2008/0071370 A1 | 3/2008 | Vinas |
| 2008/0140194 A1 | 6/2008 | Hansen |
| 2009/0177220 A1* | 7/2009 | Zimmerling et al. ......... 606/190 |
| 2010/0023122 A1 | 1/2010 | Young |
| 2011/0066237 A1* | 3/2011 | Matheny ..................... 623/2.41 |

FOREIGN PATENT DOCUMENTS

| | | |
|---|---|---|
| WO | WO 88/06877 A1 | 9/1988 |
| WO | WO 01/47452 A1 | 7/2001 |
| WO | WO 03/073978 A1 | 9/2003 |
| WO | WO 2004/010311 A1 | 1/2004 |
| WO | WO 2004/066888 A1 | 8/2004 |
| WO | WO 2006/055384 A2 | 5/2006 |
| WO | WO 2007/084285 A2 | 7/2007 |
| WO | WO 2009/015206 A1 | 1/2009 |

OTHER PUBLICATIONS

International Search Report, PCT/US2011/054333, Dated May 3, 2012.

* cited by examiner

KITS, COMPONENTS AND METHODS FOR TISSUE RECONSTRUCTION

CROSS REFERENCE TO RELATED INVENTION

This application is a continuation of PCT/US2011/054333, filed Sep. 30, 2011 which claims the benefit of U.S. Provisional Patent Application No. 61/388,944, filed Oct. 1, 2010, each of which are hereby incorporated by reference in their entirety.

BACKGROUND

The present invention relates generally to surgery, and in particular embodiments to components and component combinations useful for performing tissue reconstructive surgery, especially such surgery adapted to create an external, upstanding tissue structure such as a nipple.

Tissue reconstructive surgeries are often performed after a natural tissue structure has been damaged or surgically removed or modified due to disease, injury or other causes. One relatively common reconstructive surgery involves breast reconstruction after mastectomy or other cancer-related surgeries. A surgeon rebuilds the breast, typically so it is about the same size and shape as it was before the mastectomy. The nipple and the darker area surrounding the nipple (the areola) can also be surgically reconstructed.

Several types of breast reconstruction surgery are known. Options include a newly shaped breast with the use of a breast implant, the use of a tissue flap from the patient, or a combination of the two. Nipple and areola reconstructions are usually the final phase of breast reconstruction. This surgery is done to make the reconstructed breast resemble the original breast more closely, and is an important consideration in acceptable patient outcomes in the overall breast reconstruction surgery. It is usually done after the new breast has had time to heal, which may be several months after the original surgery.

In today's practice, the tissue used to rebuild the nipple and areola is taken from the patient, such as from the newly created breast, opposite nipple, ear, eyelid, groin, upper inner thigh or buttocks. Tattooing may be done to match the color of the nipple of the other breast and to create the areola. A challenge that arises in creating a reconstructed, upstanding nipple, is that the volume and/or height of the originally reconstructed nipple is often lost over time as the patient heals.

There remain needs in the area of tissue reconstruction for components, kits and strategies that facilitate the retention of desirable appearance qualities, such as height and/or volume, of reconstructed, upstanding external tissue structures such as nipples. In several embodiments, the present invention is addressed to these needs.

SUMMARY

Certain aspects of the present invention provide components, component combinations, kits and methods useful for creating reconstructed tissue structures, particularly those tissue structures which occur externally on a patient and are upstanding or project outwardly from surrounding tissue such as skin. Embodiments of the invention include novel surgical templates, surgical implants, and/or post-surgical shields for protecting reconstructed nipple or other upstanding tissue structures. Combinations of some or all of these components in kits also provide embodiments of the invention herein, as do methods for surgery that involve the use of some or all of these components, and methods for distributing products that involve the distribution of some or all of these components. In preferred embodiments, combinations will include a tissue-filling, remodelable implant of a selected size and at least one surgical template for creating incisions to reliably and repeatably form a patient tissue enclosure that will be beneficially conformable to the remodelable implant in order to provide good tissue apposition to the implant to promote proper patient tissue invasion and ingrowth into the implant and lasting volume infill. The remodelable implant can comprise a remodelable extracellular matrix material, such as a extracellular matrix sheet isolated in sheet form from a mammalian or other tissue source, and configured, e.g. by rolling and/or molding, to provide a shaped (e.g. generally cylindrical) implant. Kits can include implants in a plurality of sizes for selection by the physician or other health care provider, along with a plurality of templates of differing sizes, with selected templates calibrated to provide the appropriately sized enclosure for a given size of implant included in the kit. Indicia can be included on the templates or otherwise included in the kit as to which template sizes an appropriate enclosure for a given sized implant. Kits can also include a single shield sized to covering and shield a reconstructed upstanding tissue structure made using any of the implant/template combinations, or can include a plurality of shields with each sized to a given implant/template combination. Nipple reconstructions components, kits and methods form preferred embodiments of the invention.

In certain embodiments, the present disclosure provides a kit for tissue reconstruction to create a projecting tissue structure, comprising: at least one surgical template for guiding incisions for creating a patient tissue enclosure for a projecting tissue structure; and at least one reconstruction graft for receipt within the patient tissue enclosure, wherein the surgical template is calibrated to provide a conformal condition of the patient tissue enclosure around the reconstruction graft. The surgical template can be configured to guide incisions so as to create tissue flaps having opposable edges, such that when the opposable edges are brought together the tissue flaps form a void for receiving the reconstruction graft such that the inner surface of the tissue flaps is in contact with the reconstruction graft.

Additional embodiments of the invention as well as features and advantages thereof will be apparent from the descriptions herein.

DETAILED DESCRIPTION

For the purpose of promoting an understanding of the principles of the invention, reference will now be made to certain embodiments thereof and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

As disclosed above, certain aspects of the present invention provide components, component combinations, kits and methods for tissue reconstructive surgery or for distributing (e.g. by sale) products for tissue reconstructive surgery. The following discussions focus upon nipple reconstructive surgery in many aspects. It will be understood that while nipple reconstructive surgery, and products and methods therefore, form unique, preferred embodiments of the invention, the invention is also applicable to other tissue reconstructive surgeries and in particular to those for creating a structure that projects from adjacent external tissue of the patient such as skin.

Figure 1:
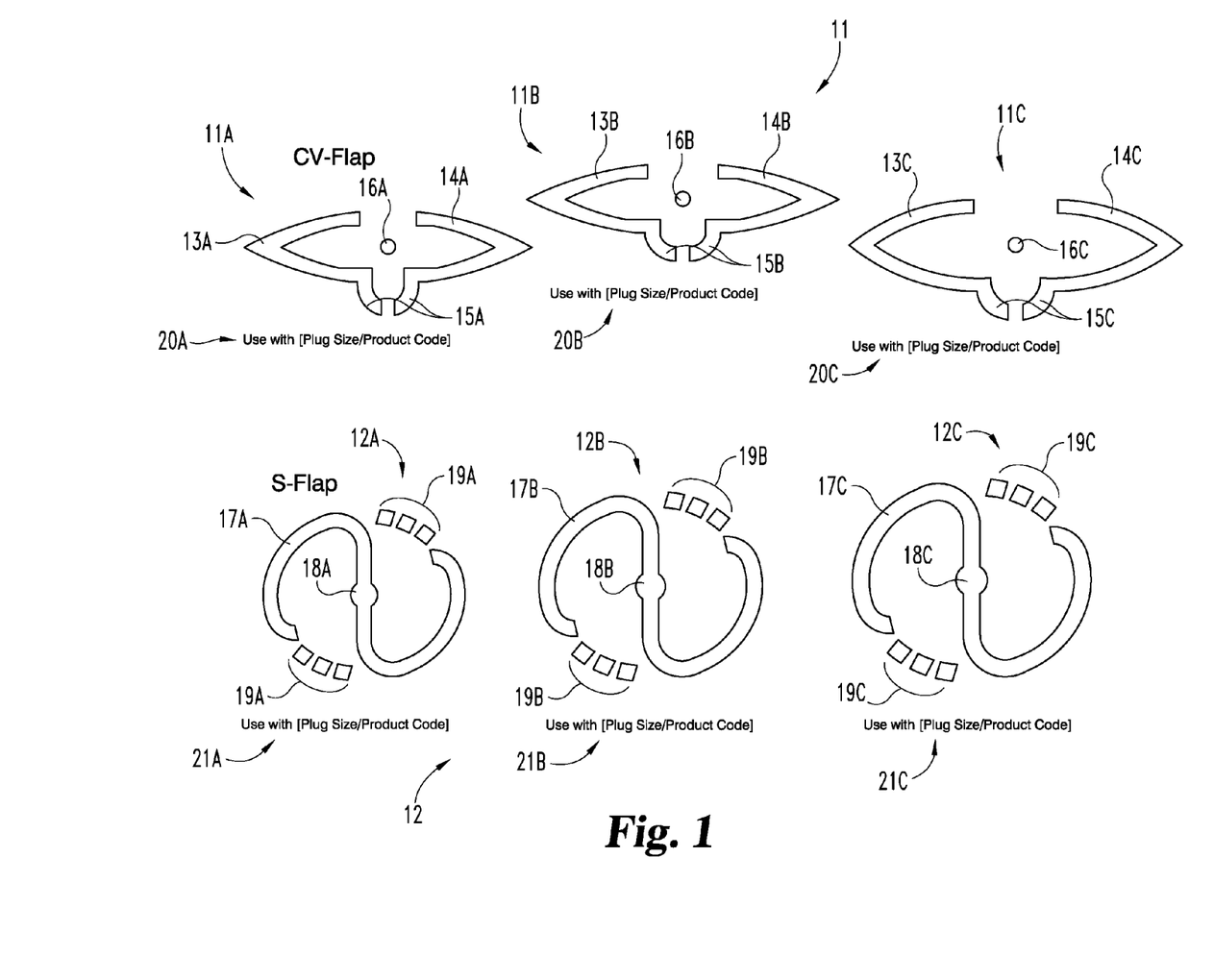
FIG. 1 provides a top view of a sheet providing surgical incision templates.

With reference to FIG. 1, shown is a top view of an illustrative multi-use marking template 10 of the invention. Template 10 includes a first region 11 containing a plurality of voids defining templates 11A, 11B, and 11C for differently-sized CV-Flap incisions for nipple reconstruction. Template 11A includes a first marking void 13A defining an incision path for a first V flap, a second marking void 14A defining an incision path for a second V-flap, and void regions 15A defining an incision path for a C flap. Separate void regions 15A are shown in the illustrated embodiment as connected to void regions 13A and 14A. It will be understood however that other arrangements will be suitable including having a separate void region for defining a C flap. Template 11A also includes a central marking void 16A which is for centering visualization by the attending physician or care provider. Templates 11B and 11C have similar voids, except differently sized. Templates 11A, 11B and 11C also have respective visually associated indicia 20A, 20B and 20C giving indication (for example, by implant size, product code, or a combination thereof) of which implant should be used with the associated template.

Multi-use template 10 also includes a region defining a plurality of marking templates 12A, 12B and 12C for performing S-flap nipple reconstruction surgery. Template 12A includes a marking void 17A defining a path for an S-shaped incision, and an enlarged, central void region 18A connected to the void 17A, with void region 18A provided for centering visualization by the physician or care provider. Template 12A also includes two sets of voids 19A which are for creating visualization markings approximating a circle when considered in combination with the outer regions of the S-void 17A, to help guide placement and use of template 17A and markings made therewith. Templates 11B and 11C have similar voids, except differently sized. Templates 12A, 12B and 12C also have respective visually associated indicia 21A, 21B and 21C giving indication (for example, by implant size, product code, or a combination thereof) of which implant should be used with the associated template.

It will be understood that while multi-use template 10 and its use constitutes an embodiment of the invention, individual templates could also be provided for templates 11A, 11B, 11C, 12A, 12B, and 12C, or multi-use templates could be provided including any number of these specific templates, or other appropriate templates. These and other variations in the provision of marking template(s) for creating patient tissue enclosures will be apparent to those of ordinary skill in the art from the descriptions herein.

Figure 2:
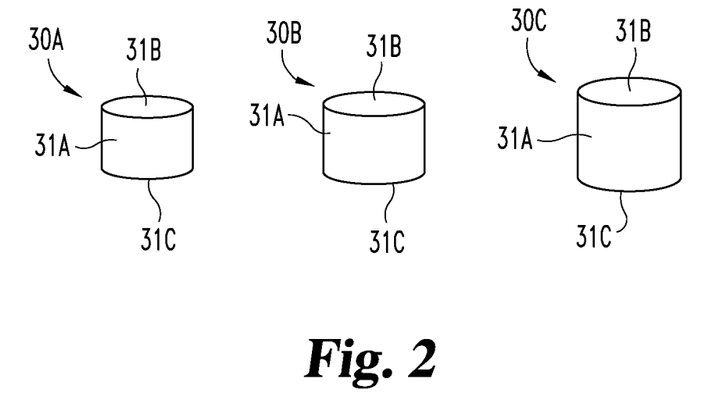
FIG. 2 provides a perspective view of a reconstructive graft.

FIG. 2 provides perspective views of variously-sized tissue reconstructive graft implants 30A, 30B and 30C. The illustrated implants are generally cylindrical in shape and preferably sized appropriately for nipple reconstructive surgery for a female breast. Illustratively, the implants can have a diameter D in the range of about 0.5 to about 1.5 cm and a height H in the range of about 0.7 to about 2 cm. Implant 30A has a generally circular cross section and a cylindrical outer wall 31A, an upper surface 31B, and a lower surface 31C. Implants 30B and 30C have similar features, which are correspondingly numbered. In combinations, including but not limited to kits and/or product literature, implant 30A can be correlated to an appropriately-sized template for use of implant 30A, for example template 11A or 12A of multi-use template 10. Implants 30B and 30C can also be correlated to respective appropriately-sized templates.

Figure 3A:
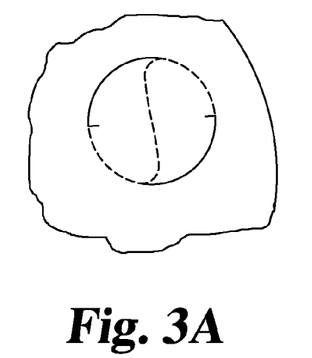
FIGS. 3A-3E provide perspective views of one embodiment of a use of a surgical template and implant of the invention.
Figure 3B:
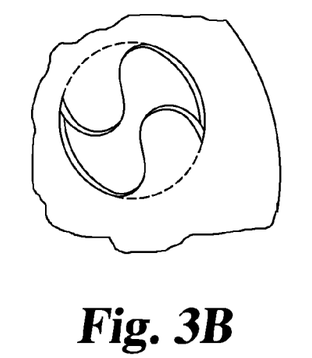
Figure 3C:
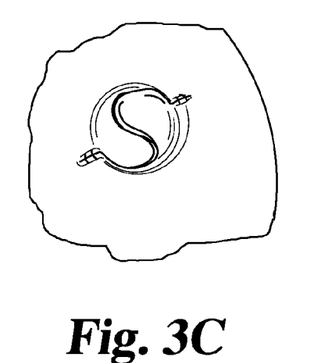
Figure 3D:
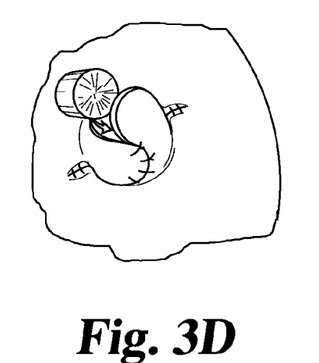
Figure 3E:
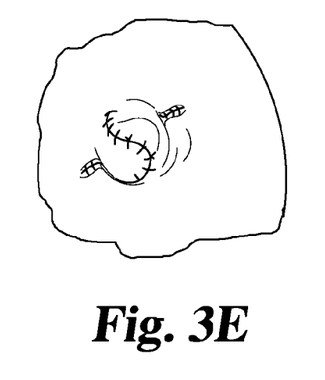

With reference to FIGS. 3A to 3E, shown are various stages of a nipple reconstruction surgery using an S-flap template and implant in accordance with the invention. In FIG. 3A, shown is a tissue mound of a reconstructed patient breast, bearing an S-shaped incision path marking and additional markings which in conjunction with the S-shaped mark approximate a circle, both made using for example a template such as 12A, 12B or 12C of FIG. 1. A dissection along the S-shaped incision is conducted to create free-moving skin flaps, and the tissue allowed to relax as shown in FIG. 3B. The tissues at point A and point B are brought together, and then the tissues at points C and D are brought together. This yields a projecting tissue enclosure structure as shown in FIG. 3C. The laterally-projecting lines of the original incision are sutured or otherwise connected together, as shown in FIG. 3C, and the S-shaped incision line formed by the apposed flaps is partially sutured or otherwise connected together, as shown in FIG. 3D. A nipple reconstruction implant, for example implant 30A, 30B or 30C of FIG. 2, is then inserted into the tissue enclosure as shown in FIG. 3D. With use of the corresponding template as discussed, the tissue enclosure created is appropriately sized to closely conform to the volume of the implant with no or essentially no dead space between the implant and patient tissue, directly apposing patient tissue against the external surface of the implant. In the preferred embodiments in which a graft implant is used that becomes invaded by and replaced by patient tissue, such as a remodelable extracellular matrix tissue graft, the apposition of patient tissue against the implant facilitates cellular invasion of the implant from the adjoining patient tissue to promote reliable patient tissue volume infill to replace the implanted material. The tissue enclosure can then be completely closed by suture or otherwise as shown in FIG. 3E. In preferred embodiments employing graft implants that become replaced by patient tissue, over time, the implant can be completely replaced by patient tissue while substantially retaining the original volume of the reconstructed nipple shown in FIG. 3E.

Figure 4A:
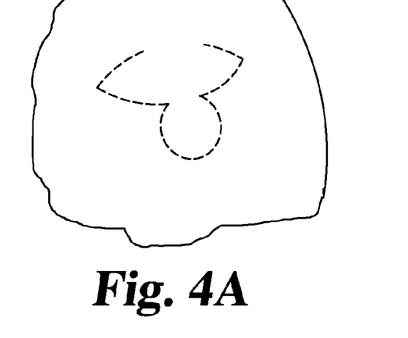
FIGS. 4A-4E provide perspective views of another embodiment of a use of a surgical template and implant of the invention.
Figure 4B:
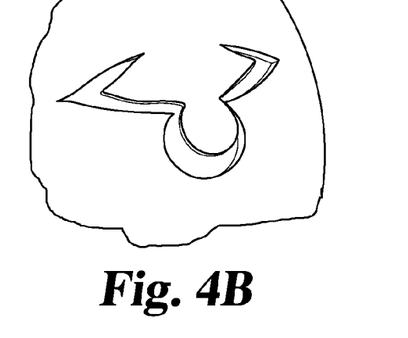
Figure 4C:
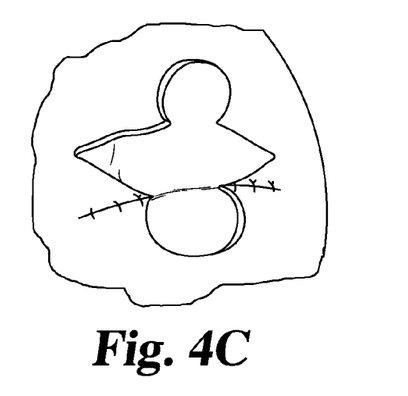
Figure 4D:
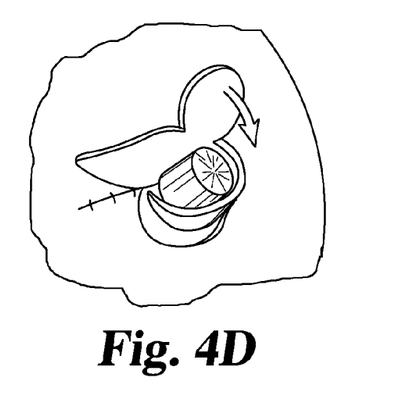
Figure 4E:
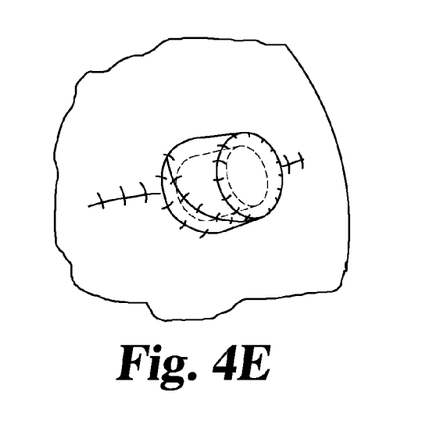

With reference to FIGS. 4A-4E, shown is set of drawings similar to those of FIGS. 3A-3E, except illustrating a nipple reconstruction using a CV-flap technique. In FIG. 4A, shown is a tissue mound of a reconstructed patient breast, bearing an CV-flap incision path marking, made using for example a template such as 11A, 11B or 11C of FIG. 1. An incision and dissection along the incision are conducted to create free-moving skin flaps, and the tissue allowed to relax, as shown in FIG. 4B. The flaps are raised and the donor area is closed by sutures or otherwise as shown in FIG. 4C, creating laterally-projecting lines of the original incision are sutured or otherwise connected together. A nipple reconstruction implant, for example implant 30A, 30B or 30C of FIG. 2, is then placed underneath the tissue flaps, and the flaps closed around the implant as shown in FIGS. 4D and 4E. To do so, the V-flaps can be first wrapped around the implant and sutured/connected in place, followed by folding the C-flap over to cap the structure and suturing/connecting it in place. Alternatively, the V-flaps can be sutured/connected together to create a cylinder, and the implant inserted in the cylinder followed by capping with the C-flap. Again, with use of the corresponding template as discussed, the tissue enclosure created is appropriately sized to closely conform to the volume of the implant with no or essentially no dead space between the implant and patient tissue, directly apposing patient tissue against the external surface of the implant. Using preferred graft implants that become invaded and replaced by patient tissue, such as remodelable extracellular matrix tissue graft implants, the apposition of patient tissue against the implant facilitates cellular invasion of the implant from the adjoining patient tissue to promote reliable patient tissue volume infill to replace the implanted material. The tissue enclosure can then be completely closed by suture or otherwise as shown in FIG. 4E. In preferred embodiments employing graft implants that become replaced by patient tissue, over time, the implant can be completely replaced by patient tissue while substantially retaining the original volume of the reconstructed nipple shown in FIG. 4E.

In either the embodiments shown in FIGS. 3A-3E or 4A-4E, the patient tissue can be connected to the implant by sutures used in closure of the enclosure, and/or by separate sutures, e.g. passed through the base of the reconstructed nipple. Such connection(s) can help to prevent migration of the implant.

Figure 5:
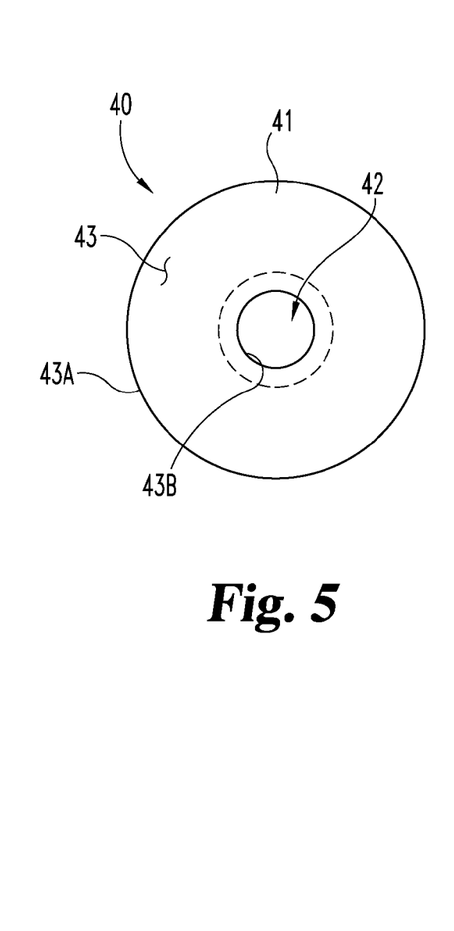
FIG. 5 provides a top view of a shield embodiment useful for shielding a reconstructed nipple.
Figure 6:
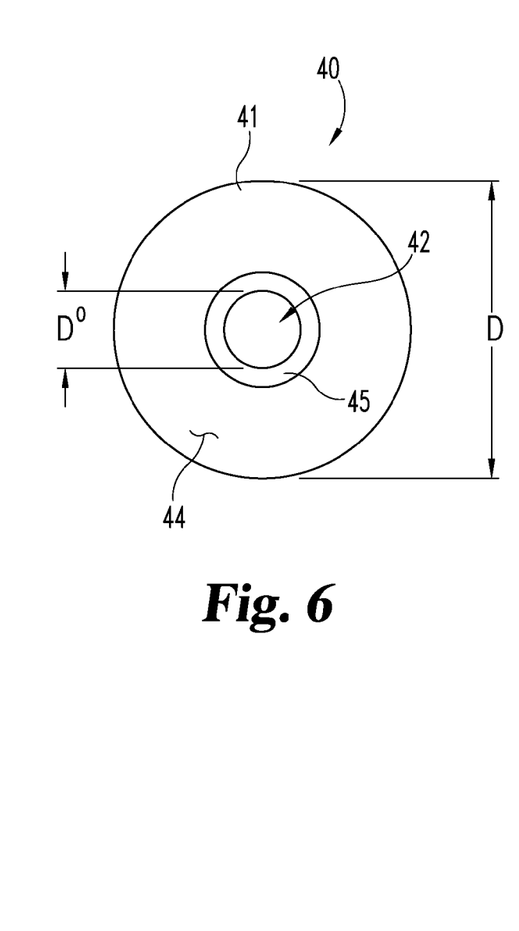
FIG. 6 provides a bottom view of the shield of FIG. 5.
Figure 7:
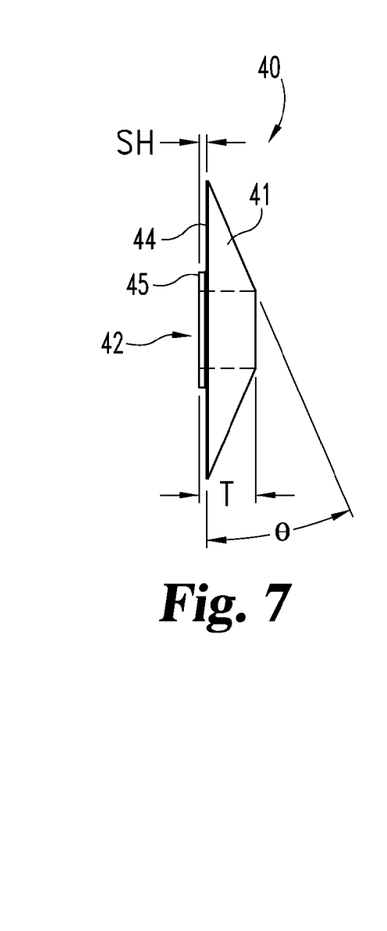
FIG. 7 provides a side view of the shield of FIG. 5.

With reference to FIGS. 5-7, shown are various views of a nipple shield 40 of and for use or inclusion in embodiments of the invention. For example, the illustrated shield 40 can be included in kits or other combinations along with templates and/or reconstruction implants as described herein, can be used in reconstruction methods as described herein, and can be distributed in conjunction with templates and/or implants as described herein. The nipple shield 40 is adapted for receipt over a reconstructed nipple and can, for example, be worn within and supported against a brazier or other clothing item and/or temporarily adhered to the skin of the patient.

Shield 40 has a generally annular body 41 that is preferably solid in cross section and defines a central opening 42 for receiving a reconstructed nipple. Body 41 has an outer surface 43 and an inner surface 44. Opening 42 opens from inner surface 44 and in preferred embodiments is a thru-hole extending completely from inner surface 44 to outer surface 43, although in alternate embodiments opening 42 can extend only partially from inner surface 44 to outer surface 43 and nonetheless provide a void suitably sized to receive the reconstructed nipple. Surfaces 43 and 44 preferably define an angle $\theta$ in the range of about 15 degrees to about 30 degrees, more preferably about 20 degrees to 25 degrees, providing for a tapering wall thickness in the annular body. Outer surface 43 preferably proceeds from a thin outer rim or edge 43A to the point of greatest thickness for shield 40, which in the illustrated embodiment is the internal rim or edge 43B, in a smooth surface without any upstanding projections. With thin rim 43A received conformably against patient tissue surrounding the reconstructed nipple, this facilitates the smooth deflection of displacement forces imparted to the shield 40 by objects, such as a brazier or other article of clothing, without catching of the shield 40 on the objects which would potentially unduly displace the position of shield 40 and thereby potentially abrade or deform a protected reconstructed nipple received within opening 42. In the preferred embodiment 40, an annular shoulder 45 is positioned around opening 42 on the inner surface 44 of the shield 40. This shoulder, adjacent to the opening 42 in which the protected nipple is received, is configured to press against sutured/connected incision line(s) occurring lateral to the reconstructed nipple. It has been reported that contraction along these lateral incision line(s) can cause the development of forces that tend to flatten the reconstructed nipple such that it loses height. By exerting pressure upon those incision lines during healing, shoulder 45 can reduce or eliminate contraction along those lines and thus help to protect the height of the protected reconstructed nipple.

Shield 40 preferably has a total thickness "T" in the range of about 8 to about 20 millimeters, more preferably in the range of about 12 to about 18 millimeters. Such thickness "T" is desirably greater than the height of the reconstructed nipple to be protected, such that the nipple is completely encompassed within opening 42. Shoulder 45 preferably has a shoulder height "SH" in the range of about 0.5 to about 4 millimeters, more preferably about 1 to about 3 millimeters. The diameter "D" of shield 40 is typically in the range of about 30 to about 100 millimeters, more preferably about 70 to about 90 millimeters. The diameter "D'" of opening 42 is typically about 15 to about 30 millimeters, more typically about 18 to about 22 millimeters. The preferred shield 40, in overall shape, is a generally flat, centrally-bored right circular cone, or quoit. Shield 40 is preferably made of a material that conforms to the breast mound around the reconstructed nipple, and most preferably a flexible or elastomeric polymeric material such as silicone.

The reconstruction implant, such as implant 30A, 30B or 30C of FIG. 2, can be made of any suitable implant material. In preferred aspects of the invention, a beneficial cooperative synergy occurs in the provision or use of a surgical template in combination with a reconstruction graft implant comprised of a material that is resorbed over time as it is replaced by patient tissue, resulting in a reconstructed nipple composed substantially or completely of patient tissue. The reliable performance of such graft materials to develop a volume of patient tissue has been found to be dependent in substantial portion upon the close apposition of patient tissue with adequate blood supply against the graft material, to promote sufficiently rapid cellular invasion for tissue development prior to resorption or degradation of the implanted material in the patient. Thus, in accordance with aspects of the invention, the use of a template that guides the surgeon to reproducibly create appropriately sized, well-perfused tissue flaps, which when arranged and connected form a closely conforming enclosure around the graft material, provides significant cooperative benefits. Still further cooperative benefits to retaining reconstructed nipple volume and/or height may be provided by the use of such graft implant/template combinations in further combination with a nipple shield that effectively protects the reconstructed graft-containing nipple and/or that compresses laterally-extending closed incisions during healing, for example shield 40 as described herein in connection with FIGS. 5-7.

Turning now to a discussion of graft materials that can be used to form the reconstructive implants, the graft materials preferably include a material that is capable upon implantation of resorbing as it is replaced by patient tissue over time. Remodelable materials that promote cellular invasion and ingrowth are preferred. Suitable such remodelable materials for use in the invention can be provided by collagenous extracellular matrix (ECM) materials, including in certain forms angiogenic collagenous ECM materials. For example, suitable collagenous materials include ECM materials isolated in an ECM sheet form that includes submucosa, renal capsule membrane, dermal collagen (including processed dermal collagen from human cadavers, which can be used as allograft in humans), dura mater, pericardium, facia lata, serosa, peritoneum, or basement membrane layers, including liver basement membrane. Suitable submucosal tissue materials for these purposes include, for instance, intestinal submucosal tissue, including small intestinal submucosal tissue, stomach submucosal tissue, urinary bladder submucosal tissue and uterine submucosal tissue. The preferred medical graft products of the invention will include submucosal tissue, such as submucosal tissue derived from a warm-blooded vertebrate. Mammalian submucosal and other ECM tissue materials are preferred. In particular, submucosal materials derived from animals raised for meat or other product production, e.g. pigs, cattle or sheep, will be advantageous. Porcine submucosal tissue provides a particularly preferred material for use in the present invention, especially porcine small intestine submucosal tissue (SIS). The submucosal or other ECM tissues can retain substantially their native cross-linking (being uncrosslinked with chemical or other effective crosslinking agents).

The submucosal or other ECM material can be derived from any suitable organ or other biological structure, including for example submucosal tissue derived from the alimentary, respiratory, intestinal, urinary or genital tracts of warm-blooded vertebrates. Submucosal tissue useful in the present invention can be obtained by harvesting such tissue sources and delaminating the submucosal tissue from smooth muscle layers, optionally also from mucosal layers and/or potentially other layers occurring in the tissue source. For additional information concerning submucosal tissue useful in certain embodiments of the present invention, and its isolation and treatment, reference can be made, for example, to U.S. Pat. Nos. 4,902,508, 5,554,389, 5,993,844, 6,206,931, and 6,099,567.

Submucosal or other ECM materials of the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination (with staining where appropriate). Such non-collagenous solids can constitute a significant percentage of the dry weight of the ECM material in certain inventive embodiments, for example at least about 1%, at least about 3%, and at least about 5% by weight in various embodiments of the invention.

The submucosal or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

As prepared and used, the submucosal tissue material or any other ECM material may optionally retain and/or otherwise include growth factors or other bioactive components native to the source tissue. For example, the submucosa or other ECM material may retain one or more growth factors with which it occurs in the source tissue, such as basic fibroblast growth factor (FGF-2), transforming growth factor beta (TGF-beta), epidermal growth factor (EGF), and/or platelet derived growth factor (PDGF). As well, submucosal or other ECM material used in certain embodiments of the invention may retain from the source tissue or otherwise include other biological materials such as heparin, heparin sulfate, hyaluronic acid, fibronectin and the like. Thus, generally speaking, the submucosal or other ECM material may retain or otherwise include a bioactive component that induces, directly or indirectly, a cellular response such as a change in cell morphology, proliferation, growth, protein or gene expression. In certain preferred embodiments of the invention, the ECM material will exhibit the capacity to promote angiogenesis.

Further, in addition or as an alternative to the inclusion of such native bioactive components, non-native bioactive components such as those synthetically produced by recombinant technology or other methods, may be incorporated into the submucosal or other ECM material. These non-native bioactive components may be naturally-derived or recombinantly produced proteins that correspond to those natively occurring in the ECM material, but perhaps of a different species (e.g. human proteins applied to collagenous ECMs from other animals, such as pigs). The non-native bioactive components may also be drug substances. Illustrative drug substances that may be incorporated into and/or onto the ECM material can include, for example, antibiotics and/or thrombus-promoting substances such as blood clotting factors, e.g. thrombin, fibrinogen, and the like. These substances may be applied to the ECM material as a premanufactured step, immediately prior to the procedure (e.g. by soaking the material in a solution containing a suitable antibiotic such as cefazolin), or during or after engraftment of the ECM material within the patient.

Submucosa or other ECM material used in certain embodiments of the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. The ECM material used in certain embodiments of the invention is preferably disinfected with an oxidizing agent, particularly a peracid, such as peracetic acid. These and additional properties of submucosa or other ECM materials taught in U.S. Pat. No. 6,206,931 may be characteristic of the submucosa used in certain embodiments of the present invention.

In certain embodiments, reconstructive implants can be formed by randomly or regularly packing (e.g. as in a rolled construct) one or more pieces of single or multilaminate ECM sheet material within a mold and thereafter processing the packed material. Such suitable processing can include, for example, providing the packed ECM sheet material in a partially or otherwise completely wetted or hydrated form and thereafter partially or completely dehydrothermally bonding the hydrated packed sheet material to establish a substantially unitary implant graft construct, or a precursor that can be cut to provide the implant graft construct. Illustratively, for example, a randomly packed graft construct can be formed by placing folded, wadded, gathered, or otherwise packed ECM sheet material within a mold, and thereafter drying (e.g. by lyophilization) the randomly configured material to form a substantially unitary graft construct. In alternative embodiments, a packed graft construct can be formed by situating randomly packed hydrated ECM material within a substantially uniform ECM sheet material, for example a tubular or planar sheet material lining all or part of a mold, and thereafter processing the configured material to form a substantially uniform construct. Illustratively, for example, the outer surface of the graft construct can be either completely or partially covered or formed using an organized material, such as one or more layers or segments of ECM sheet material. In certain embodiments, the outer surface of a packed graft construct, or portions thereof, can be varied, for example, by selectively covering only portions of the randomly packed or positioned material with an ECM sheet material. Illustratively, a packed construct can be formed by either partially or completely covering the inner surface of a mold with one or more wetted ECM sheet materials, and filling the mold cavity with wadded or gathered wetted ECM material, and thereafter drying the positioned material using any suitable drying technique as discussed herein.

Illustratively, wetted randomly or regularly packed ECM materials of the invention can occupy any suitable configuration, shape, and/or length for the reconstructive implant or precursor thereto, and can be dried using any suitable drying technique or any suitable combination thereof, including air drying, lyophilization, heated drying and others. For example, in certain embodiments, the ECM material can be packed within a mold and then dried within the mold. Alternatively, the ECM material can be packed within a mold and thereafter removed from the mold and dried. Still alternatively, a piece or pieces of ECM material can be packed within a mold, pressed or compressed within the mold, and thereafter dried, optionally while contained within the mold.

Suitable nipple reconstruction implants for use in the invention, formed as rolled, lyophilized constructs of ECM (submucosal) sheet material, are also available commercially from Cook Biotech Incorporated, West Lafayette, Ind., under the tradename Surgisis Biodesign® Nipple Reconstruction Cylinder.

In addition to reconstructive implants formed from sheet materials as discussed above, three-dimensionally stable porous matrix materials, such as resilient foam or sponge form materials, can be incorporated into reconstructive implants for use in the invention, including those which resorb and are replaced by patient tissue as discussed herein. Illustrative sponge or foam matrices will generally comprise porous, three-dimensionally stable bodies formed from suitable biocompatible matrix materials. For example, suitable biocompatible matrix materials include naturally-occurring polymers and/or synthetic polymers. More preferred sponge compositions of the invention will comprise collagen as a matrix-forming material, either alone or in combination with one or more other matrix forming materials. In general, sponge matrices useful in certain embodiments of the present invention can be formed by providing a liquid solution or suspension of a matrix-forming material, and causing the material to form a porous three-dimensionally stable structure; however, a sponge or foam material can be formed using any suitable formation method, as is known in the art.

Illustratively, in the formation of a collagenous sponge or foam material, a collagen solution or suspension can be prepared. The collagen may be derived from mammalian or other animal sources, for example, bovine, porcine or human sources, and desirably is derived from remodelable ECM materials as discussed herein. Synthetically-derived collagen may also be used. The determination of suitable collagen concentrations in the solution will be within the purview of those skilled in the art, with concentration ranges of about 0.05 g/ml to about 0.2 g/ml being typical.

Digestion of the collagen to form the collagen solution is usually carried out under acidic conditions, starting with ground, minced or otherwise comminuted collagen-containing tissue. Optionally, enzymatic digestion may be utilized using known enzymes for this purpose such as pepsin, trypsin, and/or papain. After digestion, the enzymes can be removed by suitable, known techniques.

The collagenous solution and/or suspension can be employed as a moldable or castable material in the formation of the foam or sponge. The cast material can be dried directly without chemical crosslinking or can be crosslinked with a suitable crosslinking agent and then dried. Illustrative crosslinking agents for these purposes include glutaraldehyde, formaldehyde, carbodiimides, UV irradiation, or other crosslinking agents. In preferred embodiments of the invention, the crosslinking agent will contain polar groups that impart a hydrophilic character to the final sponge matrix material. Desirably, a polyepoxide crosslinker is utilized for this purpose, especially a polyglycidyl ether compound. Suitable such compounds include ethylene glycol diglycidyl ether, available under the trade name Denacol EX810 from Nagese Chemical Co., Osaka, Japan, and glycerol polyglycidyl ether available under the trade name Denacol EX313 also from Nagese Chemical Co. Typically, polyglycidyl ethers or other polyepoxide compounds utilized in the invention will have from 2 to about 10 epoxide groups per molecule. The use of such epoxides and/or other crosslinking agents which impart polar groups and a hydrophilic character to the resulting matrix will provide for good wettability and rapid hydration and expansion of closure devices of the invention.

Preferred sources of collagen for forming sponge matrices useful in certain implant embodiments of or used in the invention include extracellular matrix materials such as collagenous submucosal tissues, and other collagenous basement membrane materials. These include, for example, small intestinal submucosa, stomach submucosa, urinary bladder submucosa, liver basement membrane, and other basement membrane materials. For additional information as to these collagenous matrix materials and their preparation, reference can be made for example to U.S. Pat. Nos. 4,511,653, 4,902,508, 4,956,178, 5,554,389, and 6,099,567, and International Publication Nos. WO9825637 and WO9822158, each of which is hereby incorporated herein by reference in its entirety. In forming sponge matrices, these materials are preferably processed and utilized under conditions which retain their favorable growth properties. This may include, for example, processing under conditions in which native proteins and/or other materials, for instance biotropic agents, are retained in their bioactive form. For example, the collagen sources, and resulting sponge matrices, may include active native substances such as one or more growth factors, e.g. basic fibroblast growth factor (FGF-2); transforming growth factor beta (TGF-beta); epidermal growth factor (EFG); platelet derived growth factor (PDGF); and/or other substances such as glycosaminoglycans (GAGs); and/or fibronectin (FN).

In additional embodiments, resorbable reconstructive implants that are replaced by patient tissue can be made from ECM's or other collagenous materials that have been subjected to processes that expand the materials. In certain forms, such expanded materials can be formed by the controlled contact of an ECM material with one or more alkaline substances until the material expands, and the isolation of the expanded material. Illustratively, the contacting can be sufficient to expand the ECM material to at least 120% of (i.e. 1.2 times) its original bulk volume, or in some forms to at least about two times its original volume. Thereafter, the expanded material can optionally be isolated from the alkaline medium, e.g. by neutralization and/or rinsing. The collected, expanded material can be used in any suitable manner in the preparation of a graft device. Illustratively, the expanded material can be enriched with bioactive components, dried, and/or molded, etc., in the formation of a graft construct of a desired shape or configuration.

Expanded collagenous or ECM materials can be formed for example by the controlled contact of a collagenous or ECM material with an aqueous solution or other medium containing sodium hydroxide or other denaturing agent. Alkaline treatment of the material can cause changes in the physical structure of the material that in turn cause it to expand. Such changes may include denaturation of the collagen in the material. In certain embodiments, it is preferred to expand the material to at least about three, at least about four, at least about 5, or at least about 6 or even more times its original bulk volume. The magnitude of the expansion is related to several factors, including for instance the concentration or pH of the alkaline medium, exposure time, and temperature used in the treatment of the material to be expanded.

ECM materials that can be processed to make expanded materials can include any of those disclosed herein or other suitable ECM's. Typical such ECM materials will include a network of collagen fibrils having naturally-occurring intramolecular cross links and naturally-occurring intermolecular cross links. Upon expansion processing as described herein, the naturally-occurring intramolecular cross links and naturally-occurring intermolecular cross links can be retained in the processed collagenous matrix material sufficiently to maintain the collagenous matrix material as an intact collagenous sheet material; however, collagen fibrils in the collagenous sheet material can be denatured, and the collagenous sheet material can have an alkaline-processed thickness that is greater than the thickness of the starting material, for example at least 120% of the original thickness, or at least twice the original thickness.

Illustratively, the concentration of the alkaline substance for treatment of the remodelable material can be in the range of about 0.5 to about 2 M, with a concentration of about 1 M being more preferable. Additionally, the pH of the alkaline substance can in certain embodiments range from about 8 to about 14. In preferred aspects, the alkaline substance will have a pH of from about 10 to about 14, and most preferably of from about 12 to about 14.

In addition to concentration and pH, other factors such as temperature and exposure time will contribute to the extent of expansion, as discussed above. In this respect, in certain variants, the exposure of the collagenous material to the alkaline substance is performed at a temperature of about 4 to about 45° C. In preferred embodiments, the exposure is performed at a temperature of about 25 to about 40° C., with 37° C. being most preferred. Moreover, the exposure time can range from at least about one minute up to about 5 hours or more. In some embodiments, the exposure time is about 1 to about 2 hours. In a particularly preferred embodiment, the collagenous material is exposed to a 1 M solution of NaOH having a pH of 14 at a temperature of about 37° C. for about 1.5 to 2 hours. Such treatment results in collagen denaturation and a substantial expansion of the remodelable material. Denaturation of the collagen matrix of the material can be observed as a change in the collagen packing characteristics of the material, for example a substantial disruption of a tightly bound collagenous network of the starting material. A non-expanded ECM or other collagenous material can have a tightly bound collagenous network presenting a substantially uniform, continuous surface when viewed by the naked eye or under moderate magnification, e.g. 100× magnification. Conversely, an expanded collagenous material can have a surface that is quite different, in that the surface is not continuous but rather presents collagen strands or bundles in many regions that are separated by substantial gaps in material between the strands or bundles when viewed under the same magnification, e.g. about 100×. Consequently, an expanded collagenous material typically appears more porous than a corresponding non-expanded collagenous material. Moreover, in many instances, the expanded collagenous material can be demonstrated as having increased porosity, e.g. by measuring for an increased permeability to water or other fluid passage as compared to the non-treated starting material. The more foamy and porous structure of an expanded ECM or other collagenous material can allow the material to be cast or otherwise prepared into a variety of sponge or foam shapes for use in the preparation of reconstructive implants herein After such alkaline treatments, the material can be isolated from the alkaline medium and processed for further use. Illustratively, the collected material can be neutralized and/or rinsed with water to remove the alkalinity from the material, prior to further processing of the material to form a graft construct.

A starting ECM material (i.e., prior to treatment with the alkaline substance or other collagen-denaturing agent) can optionally include a variety of bioactive or other non-collagenous components including, for example, growth factors, glycoproteins, glycosaminoglycans, proteoglycans, nucleic acids, and lipids. Treating the material with an alkaline substance may reduce the quantity of one, some or all of such non-collagenous components contained within the material. In certain embodiments, controlled treatment of the remodelable material with an alkaline substance will be sufficient to create a remodelable collagenous material which is substantially devoid of nucleic acids and lipids, and potentially also of growth factors, glycoproteins, glycosaminoglycans, and proteoglycans.

In certain embodiments, one or more bioactive components, exogenous or endogenous, for example, similar to those removed from an expanded material during alkaline processing, can be returned to the material. For example, an expanded material can include a collagenous material which has been depleted of nucleic acids and lipids, but which has been replenished with growth factors, glycoproteins, glycosaminoglycans, and/or proteoglycans. These bioactive components can be returned to the material by any suitable method. For instance, in certain forms a tissue extract, such as is discussed in U.S. Pat. No. 6,375,989 which is hereby incorporated herein by reference in its entirety, containing these components can be prepared and applied to an expanded collagenous material. In one embodiment, the expanded collagenous material can be incubated in a tissue extract for a sufficient time to allow bioactive components contained therein to associate with the expanded collagenous material. The tissue extract may, for example, be obtained from non-expanded collagenous tissue of the same type used to prepare the expanded material. Other means for returning or introducing bioactive components to an expanded remodelable collagenous material include spraying, impregnating, dipping, etc. as known in the art. By way of example, an expanded collagenous material may be modified by the addition of one or more growth factors such as basic fibroblast growth factor (FGF-2), transforming growth factor beta (TGF beta), epidermal growth factor (EGF), platelet derived growth factor (PDGF), and/or cartilage derived growth factor (CDGF). As well, other biological components may be added to an expanded collagenous material, such as heparin, heparin sulfate, hyaluronic acid, fibronectin and the like. Thus, generally speaking, an expanded collagenous material may include a bioactive component that induces, directly or indirectly, a cellular response such as a change in cell morphology, proliferation, growth, protein or gene expression.

Expanded collagenous materials can be used to prepare a wide variety of nipple or other reconstructive implants. Methods for preparing such implants can include contacting an ECM or other collagenous starting material with an alkaline substance or other collagen-denaturing substance in an amount effective to expand the material, casting or otherwise forming the expanded collagenous material into an implant shape (e.g. generally cylindrical as described herein), and lyophilizing the expanded material to form a dried implant device All publications cited herein are hereby incorporated by reference in their entirety as if each had been individually incorporated by reference and fully set forth.

The use of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A kit for tissue reconstruction to create a projecting tissue structure, comprising:
    at least one surgical template for guiding incisions for creating a patient tissue enclosure for a projecting tissue structure; and
    at least one reconstruction graft for receipt within the patient tissue enclosure, wherein the surgical template is calibrated to provide a conformal condition of the patient tissue enclosure around the reconstruction graft, wherein said surgical template is configured to guide incisions so as to create tissue flaps having opposable edges, such that when the opposable edges are brought together the tissue flaps form a void for receiving said reconstruction graft such that the inner surface of the tissue flaps is in contact with said reconstruction graft.

2. The kit of claim 1, wherein said projecting tissue structure comprises a reconstructed nipple.

3. The kit of claim 1, wherein the reconstruction graft comprises remodelable extracellular matrix tissue.

4. The kit of claim 2, wherein the reconstruction graft further comprises a rolled remodelable extracellular matrix sheet material.

5. The kit of claim 2, also comprising a nipple shield configured to receive and shield the reconstructed nipple.

6. The kit of claim 5, wherein the shield includes an opening for receipt over the reconstructed nipple and one or more projecting shoulder portions adjacent the opening.

7. The kit of claim 6, wherein said shield includes an annular shoulder around said opening.

8. The kit of claim 6, wherein the shield has an inner surface and an outer surface, with said opening extending from said inner surface to said outer surface.

9. The kit of claim 6, wherein the shield has an annular body defining said opening in a central region thereof, wherein said annular body has a tapered wall thickness extending from an outer rim to said opening.

10. The kit of claim 9, wherein said opening is a thru-hole in said body, and wherein said outer surface continuously tapers from an outer rim to a point of greatest thickness of the body.

11. The kit of claim 10, wherein said point of greatest thickness is an inner rim bounding said thru-hole.

12. The kit of claim 8, wherein said outer surface presents a conical shape extending from an outer rim to said opening.

13. The kit of claim 1, said reconstruction graft having an outer surface, and wherein said patient tissue enclosure is sized to conform to the volume of the reconstruction graft and directly contact the external surface of the reconstruction graft.

14. A method for creating a reconstructed nipple, comprising:
    marking patient tissue in a region for creation of a reconstructed nipple using a surgical template for creating markings to guide incisions for creating a patient tissue enclosure, wherein the surgical template is configured to guide incisions so as to create tissue flaps having opposable edges, such that when the opposable edges are brought together the tissue flaps form a void for receiving a reconstruction graft such that the inner surface of the tissue flaps is in contact with the reconstruction graft;
    incising the marked patient tissue so as to create tissue flaps having opposable edges;
    bringing the opposable edges together such that the tissue flaps form a void; and implanting a nipple reconstruction graft in the void created from the incised patient tissue, with the inner surface of the tissue flaps in contact with the nipple reconstruction graft.

15. A method for distributing products for nipple reconstruction surgery, comprising:
   distributing a surgical marking template adapted to guide marking of patient tissue to create a patient tissue enclosure for receipt of a nipple reconstruction implant, wherein the surgical template is configured to guide incisions so as to create tissue flaps having opposable edges, such that when the opposable edges are brought together the tissue flaps form said patient tissue enclosure; and
   distributing a nipple reconstruction implant sized for receipt within said patient tissue enclosure such that the inner surface of the tissue flaps is in contact with said reconstruction implant.

* * * * *